United States Patent
Matsushita

(10) Patent No.: US 6,825,373 B2
(45) Date of Patent: Nov. 30, 2004

(54) METHOD OF PREPARING PYRROLOTRIAZIN-4-ONE COMPOUND AND METHOD OF PREPARING ISOTHIOCYANATOFORMIC ACID ESTER DERIVATIVE THAT IS A REACTANT USED FOR PREPARING PYRROLOTRIAZIN-4-ONE COMPOUND

(75) Inventor: Tetsunori Matsushita, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/074,014

(22) Filed: Feb. 14, 2002

(65) Prior Publication Data
US 2002/0128479 A1 Sep. 12, 2002

Related U.S. Application Data

(62) Division of application No. 09/858,723, filed on May 17, 2001.

(30) Foreign Application Priority Data

May 18, 2000 (JP) ........................................ 2000-146506
May 18, 2000 (JP) ........................................ 2000-146749

(51) Int. Cl.$^7$ ............................................ C07C 333/04
(52) U.S. Cl. ............................ 558/9; 558/233; 558/234
(58) Field of Search ............................... 558/9, 233, 234

(56) References Cited

U.S. PATENT DOCUMENTS 3,836,541 A   9/1974   Johnson et al.
4,659,853 A * 4/1987   Fu et al. .................... 558/233

FOREIGN PATENT DOCUMENTS

JP    10-316654    12/1998
JP    2001-130144   5/2001

OTHER PUBLICATIONS

Takiguchi et al., JP 5014631.*
Syntheses; H. Wamhoff et al.; Heterocyclische β–Enaminoester; 18 .Zur Synthese Von 2–Aminopyrrol–3Carbonsaure–Derivaten'; Jan. 1976; p. 51.
J.C.S. Perkin; P.R. Atkins, et al.; "Heterocyclic Syntheses with Isothiocyanatoformic Esters and Their Derivatives"; (1973).

* cited by examiner

*Primary Examiner*—Venkataraman Balasubramanian
(74) *Attorney, Agent, or Firm*—Sughrue Mion, PLLC

(57) ABSTRACT

A method of preparing a pyrrolotriazin-4-one and a method of preparing the isothiocyanatoformic acid ester derivative which can be used as a reactant in that method of preparing a pyrrolotriazin-4-one. The method of preparing the pyrrolotriazin-4-one includes an addition step of an aminopyrrole derivative and the isothiocyanatoformic compound and a step of ring-closing reaction of a resulting adduct.

14 Claims, No Drawings

METHOD OF PREPARING PYRROLOTRIAZIN-4-ONE COMPOUND AND METHOD OF PREPARING ISOTHIOCYANATOFORMIC ACID ESTER DERIVATIVE THAT IS A REACTANT USED FOR PREPARING PYRROLOTRIAZIN-4-ONE COMPOUND

This is a divisional of Application No. 09/858,723 filed May 17, 2001; the disclosure of which is incorporated herein by reference.

BACKGROUND OF THE INVENTION

1. Field of the Invention

The present invention relates to a method of preparing a pyrrolotriazin-4-one compound and, more particularly, to a method of producing a pyrrolotriazin-4-one compound which includes a step of addition reaction between a thioisocyanate compound and a 2-aminopyrrole derivative and a step of ring-closing reaction of a resulting adduct. The present invention also relates to a method of preparing an isothiocyanatoformic acid ester derivative, which is preferably used in the preparation of pyrrolotriazinone compounds.

2. Description of the Related Art

It has been known that compounds having a pyrrolotriazin-4-one skeleton are useful for use in photosensitive materials, heat-sensitive materials, color developing components in photographic materials, and precursors of biologically active substances. Various derivatives have been synthesized.

Isothiocyanatoformic acid ester derivatives have been used as reactants in the synthesis of pyrrolotriazinone compounds. It has been known that isothiocyanatoformic acid ester derivatives can be synthesized by a procedure described in J. C. S. Perkin I, page 2644 (1973). A preparation scheme of an isothiocyanatoformic acid ester derivative as described in the reference is shown below.

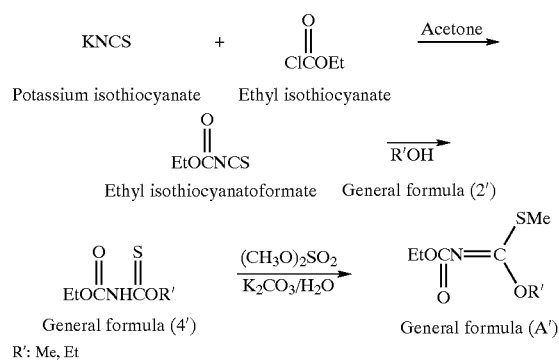

In the conventional preparation method described above, a hydroxy derivative represented by the general formula (2') is added to ethyl isothiocyanatoformate that has been formed by reacting potassium isothiocyanate with ethyl chloroformate. However, a portion of the ethyl isothiocyanatoformate decomposes before reacting with the hydroxy derivative represented by the general formula (2'), because reactivity between potassium isothiocyanate and ethyl chloroformate is high and the ethyl isothiocyanatoformate that is formed is unstable. As a result, there arises a problem that unreacted hydroxy derivative remains, thereby lowering purity and yield of an intermediate represented by the general formula (4').

The intermediate represented by the general formula (4') and the isothiocyanatoformic acid ester derivative represented by the general formula (A') (in which R' represents a methyl group or an ethyl group) must be purified by crystallization at a low temperature, that is, lower than −50° C. because of low melting points thereof. Therefore, there arises a problem that it is difficult to industrially produce the intermediate and the isothiocyanatoformic acid ester derivative at high purity and high yield because of complexity of operations.

There is also a problem that, in cases where the number of carbon atoms of R' in the intermediate represented by the general formula (4') and the isothiocyanatoformic acid ester derivative represented by the general formula (A') is 3 or more, the intermediate and the derivative are often in the form of oils. Therefore, it is difficult to industrially produce the same at high purity and high yield in this respect also.

Also, problems arise because the isothiocyanatoformic acid ester derivative represented by the general formula (A') prepared by the conventional preparation method described above has low purity, ranging from 50 to 60%, and tar components derived from by-products in the preparation of the isothiocyanatoformic acid ester derivative are formed when pyrrolotriazin-4-one is synthesized using the isothiocyanatoformic acid ester derivative as a reactant without purifying. Consequently, operation properties and the yield of pyrrolotriazin-4-one are lowered.

SUMMARY OF THE INVENTION

An object of the present invention is to provide a novel method of preparing a pyrrolotriazin-4-one compound, which method is capable of synthesizing a-compound having a pyrrolotriazin-4-one skeleton at high yield in a simple operation. Another object of the present invention is to provide a novel isothiocyanatoformic acid ester derivative, which can be used preferably as a reactant for synthesis of a pyrrolotriazinone compound, and to provide a method of preparing the isothiocyanatoformic acid ester derivative at high purity and high yield.

A means for solving the problems described above is as follows.

A method of preparing a pyrrolotriazin-4-one represented by the following general formula (4). The method includes:

an addition step of reacting an aminopyrrole derivative represented by the following general formula (1) with a reactant represented by the following general formula (2) to form an adduct represented by the following general formula (3), and a cyclization step of cyclizing the adduct represented by the following general formula (3) to form the pyrrolotriazin-4-one represented by the following general formula (4).

General formula (1)

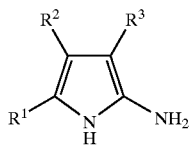

General formula (2)

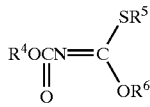

General formula (3)

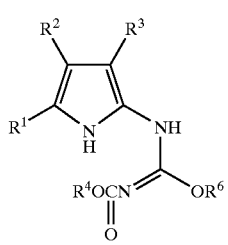

General formula (4)

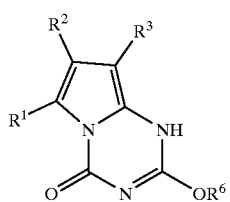

In the formulas; $R^1$ represents a hydrogen atom, an alkyl group, an aryl group, or a group capable of withdrawing. $R^2$ and $R^3$ each independently represents a hydrogen atom, an alkyl group, an aryl group, a cyano group, a substituted sulfonyl group, a substituted carbonyl group, or a halogen atom. $R^4$ and $R^6$ each independently represents an alkyl group or an aryl group. $R^5$ represents an alkyl group, an aryl group, or a heterocyclic group.

Also provided is a method of preparing an isothiocyanatoformic acid ester derivative represented by the following general formula (2). The method includes a step of adding a chloroformic acid derivative represented by the following general formula (7) to an isothiocyanic acid salt represented by the following general formula (5) and a hydroxy derivative represented by the following general formula (6) to prepare an intermediate represented by the following general formula (8):

ZNCS           General formula (5)

$R^6$OH           General formula (6)

General formula (7)

General formula (8)

Z represents a sodium atom or a potassium atom in the general formula (5). $R^4$ and $R^6$ in the general formulas (6), (7) and (8) are as defined for the general formula (2).

Further provided is a method of preparing the isothiocyanatoformic acid ester derivative represented by the general formula (2). This method includes a step of preparing an intermediate represented by the following general formula (10) from an intermediate represented by the following general formula (8) and a compound represented by the following general formula (9).

General formula (8)

General formula (9)

$M(OH)_n$

General formula (10)

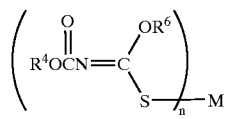

M represents an alkali metal atom, an alkali earth metal atom, an aluminum atom, or a magnesium atom in the general formula (9) $R^4$ and $R^6$ in general formula (10) are as defined in the general formula (2).

Another method of preparing the isothiocyanatoformic acid ester derivative represented by the general formula (2) includes a step of reacting an intermediate represented by the following general formula (10) with an alkylating agent represented by the following general formula (12) to prepare the isothiocyanatoformic acid ester derivative represented by the general formula (2).

General formula (10)

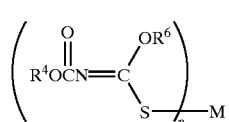

$R^5X$           General formula (11)

$(R^5O)_2SO_2$           General formula (12)

X represents a halogen atom or $SO_3Ar$ in the general formula (11). Ar represents a substituted or non-substituted aryl group. $R^5$ in the general formulas (11) and (12) is the same as that in the general formula (2).

DETAILED DESCRIPTION OF THE PREFERRED EMBODIMENTS

One mode of the present invention is a method of preparing a pyrrolotriazin-4-one compound represented by general formula (4), the same being a target substance and a 2-aminopyrrole derivative represented by the general formula (1) being a starting substance.

Another mode of the present invention is an isothiocyanatoformic acid ester derivative represented by general formula (2). The isothiocyanatoformic acid ester derivative is preferably used as a reactant in the preparation of the pyrrolotriazinone compound. For example, when the isothiocyanatoformic acid ester derivative represented by the general formula (2) in the present invention is added as a reactant, the pyrrolotriazin-4-one can be prepared by an addition reaction and a cyclization reaction.

In the general formulas (1) to (4), $R^1$ represents a hydrogen atom, an alkyl group, an aryl group, or a group capable of withdrawing; and $R^2$ and $R^3$ each independently represents a hydrogen atom, an alkyl group, an aryl group, a cyano group, a substituted sulfonyl group, a substituted carbonyl group, or a halogen atom.

Alkyl groups having a substituent and non-substituted alkyl groups are included in examples of the alkyl group represented by each of $R^1$ to $R^3$. The alkyl group may be straight-chain or branched, and may have an unsaturated bond. Examples of the substituent in cases where the alkyl group has a substituent include an alkoxy group, aryloxy group, alkoxycarbonyl group, aryloxycarbonyl group, aryl group, hydroxy group, and a halogen atom. An aryl group that is the substituent may be further substituted with an alkyl group, an alkoxy group, a nitro group, a cyano group, a hydroxy group, or a halogen atom.

Examples of the alkyl group represented by each of $R^1$ to $R^3$ include a methyl group, trifluoromethyl group, ethyl group, butyl group, hexyl group, octyl group, 2-ethylhexyl group, decyl group, dodecyl group, octadecyl group, propyl group, isopropyl group, isobutyl group, sec-butyl group, t-butyl group, pentyl group, 1-ethylpentyl group, cyclopentyl group, cyclohexyl group, isopentyl group, heptyl group, nonyl group, undecyl group, propenyl group, heptadecenyl group, t-octyl group ethoxycarbonylmethyl group, butoxycarbonylmethyl group, 2-ethylhexyloxycarbonylmethyl group, 1-(ethoxy carbonyl)ethyl group, 2',4'-diisopentylphenyloxymethyl group, 2',4'-di-t-butylphenyloxymethyl group, ethoxycarbonylethyl group, 2-ethylhexyloxycarbonyl group, butyldecyloxycarbonylethyl group, dibutylaminocarbonylmethyl group, dibenzylaminocarbonylethyl group, ethyloxycarbonylpropyl group, 2-ethylhexyloxycarbonylpropyl group, 2,4-di-t-aminophenyloxypropyl group, 1-(2',4'-di-t-aminophenyloxy)propyl group, 2,4-di-t-butylphenyloxypropyl group, acetylaminoethyl group, N,N-dihexylaminocarbonylethyl group, 2,4-di-t-amyloxyethyloxycarbonylpropyl group, isostearyloxycarbonylpropyl group, 1-(2,4-di-t-pentylphenyloxy)propyl group, 2,4-di-t-pentylphenyloxyethyloxycarbonylpropyl group, naphthyloxyethyloxycarbonylethyl group, N-methyl-N-phenylethyloxycarbonylethyl group, and methanesulfonylaminopropyl group and the like.

Examples of the aryl group represented by each of $R^1$ to $R^3$ include aryl groups having a substituent and non-substituted aryl groups. Examples of the substituent in cases where the aryl group has a substituent include an alkyl group, alkoxy group, aryloxy group, halogen atom, nitro group, cyano group, substituted carbamoyl group, substituted sulfamoyl group, substituted amino group, substituted oxycarbamoyl group, substituted oxysulfonyl group, alkylthio group, arylthio group, alkylsulfonyl group, arylsulfonyl group, aryl group, hydroxy group, acyl group, acyloxy group, substituted sulfonyloxy group, substituted aminocarbonyloxy group, and substituted phosphoryloxy group.

Examples of the aryl group represented by each of $R^1$ to $R^3$ include a phenyl group, 2-methylphenyl group, 2-chlorophenyl group, 2-methoxyphenyl group, 2-ethoxyphenyl group, 2-propoxyphenyl group, 2-isopropoxyphenyl group, 2-butoxyphenyl group, 2-(2-ethylhexyloxy)phenyl group, 2-octyloxyphenyl group, 2-undecyloxyphenyl group, 2-trifluoromethylphenyl group, 2-(2-ethylhexyloxy)-5-chlorophenyl group, 2,2'-hexyloxy-3,5-dichlorophenyl group, 3-(2,4-di-t-pentylphenoxyethoxy)phenyl group, 2-(dibutylaminocarbonylethoxy)phenyl group, 2,4-dichlorphenyl group, 2,5-dichlorophenyl group, 2,4,6-trimethylphenyl group, 3-chlorophenyl group, 3-nitrophenyl group, 3-cyanophenyl group, 3-trifluoromethylphenyl group, 3-methoxyphenyl group, 3-ethoxyphenyl group, 3-butoxyphenyl group, 3-(2'-ethylhexyloxy)phenyl group, 3,4-dichlorophenyl group, 3,5-dichlorophenyl group, 3,4-dimethoxyphenyl group, 3,5-dibutoxyphenyl group, 3-octyloxyphenyl group, 3-(dibutylaminocarbonylmethoxy) phenyl group, 3-(di-2-ethylhexylaminocarbonylmethoxy) phenyl group, 3-dodecyloxyphenyl group, 4-chlorophenyl group, 4-cyanophenyl group, 4-nitrophenyl group, 4-trifluoromethylphenyl group, 4-methoxyphenyl group, 4-ethoxyphenyl group, 4-isopropoxyphenyl group, 4-butoxyphenyl group, 4-(2-ethylhexyloxy)phenyl group, 4-isopentyloxyphenyl group, 4-(octadecyloxy)phenyl group, 4-benzylphenyl group, 4-aminosulfonylphenyl group, 4,-N,N-dibutylsulfonylphenyl group, 4-ethoxycarbonylphenyl group, 4-(2-ethylhexyloxycarbonyl)phenyl group, 4-t-octylphenyl group, 4-fluorophenyl group, 3-acetylphenyl group, 2-acetylaminophenyl group, 2,4-di-t-pentylphenyl group, 4-(2-ethylhexyloxy)carbonylphenyl group, 4-methylthiophenyl group, 4-(4-chlorophenylthio)phenyl, and hydroxyphenyl group, phenylsulfonylphenyl group, phenylsulfonyloxyphenyl group, phenylcarbonyloxyphenyl group, dimethylaminocarbonyloxyphenyl group, butylcarbonyloxyphenyl group and the like.

A group capable of withdrawing as represented by $R^1$ (hereinafter referred merely to as an "withdrawing group") means a group capable of withdrawing when the compound represented by the general formula (4) is reacted with another compound, for example, an oxide or the like of a color developing agent, such as an aromatic primary amine. The withdrawing group is a halogen atom; an aromatic azo group; an alkyl group capable of linking at a coupling position via an oxygen, nitrogen, sulfur or carbon atom; an aryl group or heterocyclic group; an alkyl or arylsulfonyl group; an arylsulfinyl group; an alkylaryl or heterocyclic carbonyl group; or a heterocyclic group capable of linking at a coupling position via a nitrogen atom. Examples thereof include a halogen atom, alkoxy group, aryloxy group, acyloxy group, alkyl or arylsulfonyloxy group, acylamino group, alkyl or arylsulfonamide group, alkoxycarbonyloxy group, aryloxycarbonyloxy group, alkylaryl or heterocyclic thio group, carbamoylamino group, arylsulfinyl group, arylsulfonyl group, five- or six-membered nitrogen-containing heterocyclic group, imide group, arylazo group and the like. An alkyl group, aryl group or heterocyclic group contained in the withdrawing group may be further substituted with a substituent. In a case of substitution with two or more substituents, the substituents may be the same or different and the substituents may further have substituents.

More specifically, preferred withdrawing groups are a halogen atom (e.g. fluorine atom, chlorine atom, bromine atom) alkoxy group (e.g. ethoxy, dodecyloxy, methoxyethylcarbamoylethoxy, carboxypropyloxy, methylsulfonylethoxy, ethoxycarbonylmethoxy), aryloxy group (e.g. 4-methylphenoxy, 4-chlorophenoxy, 4-methoxyphenoxy, 4-carboxyphenoxy, 3-ethoxycarboxyphenoxy, 3-acetylaminophenoxy, 2-carboxyphenoxy), acyloxy group (e.g. acetoxy, tetradecanoyloxy, benzoyloxy), alkyl or arylsulfonyloxy group (e.g. methanesulfonyloxy, toluenesulfonyloxy), acylamino group (e.g. dichloroacetylamino, heptafluorobutyrylamino), alkyl or arylsulfonamide group (e.g. methanesulfonamino, trifluoromethanesulfonamino, p-toluenesulfonylamino), alkoxycarbonyloxy group (e.g. ethoxycarbonylxy, benzyloxycarbonyloxy), aryloxycarbonyloxy group (e.g. phenoxycarbonyloxy), alkylaryl or heterocyclic thio group (e.g. ethylthio, 2-carboxyethylthio, dodecylthio, 1-carboxydodecylthio, phenylthio, 2-butoxy-5-t-octylphenylthio, tetrazolylthio), arylsulfonyl group (e.g. 2-butoxy-5-tert-octylphenylsulfonyl), arylsulfinyl group (e.g. 2-butoxy-5-tert-octylphenylsulfinyl), carbamoylamino group (e.g. N-methylcarbamoylamino, N-phenylcarbamoylamino), five- or six-membered nitrogen-contaning heterocyclic group (e.g. imidazolyl, pyrazolyl, triazolyl, tetrazolyl, 1,2-dihydro-2-oxo-1-pyridyl), imide group (e.g. succinimide, hydantoinyl), and arylazo group (e.g. phenylazo, 4-methoxyphenylazo) and the like. These groups may be further substituted. Examples of the withdrawing group linked through a carbon atom include a bis-type coupler obtained by condensing a 4 eq. coupler with an aldehyde or ketone. The withdrawing group may contain a photographically advantageous group such as a developing inhibitor, a developing accelerator and the like.

The withdrawing group is preferably a halogen atom, an alkoxy group, an aryloxy group, an alkyl or arylthio group, an arylsulfonyl group, an arylsulfinyl group, or a five- or six-membered nitrogen-containing heterocyclic group capable of linking at the coupling position via a nitrogen atom, and is particularly preferably an arylthio group.

Alkylsulfonyl, arysulfonyl and sulfamoyl groups are included in examples of the substituted sulfonyl group represented by each of $R^2$ and $R^3$.

Examples of the alkylsulfonyl group include a methylsulfonyl group, ethylsulfonyl group, propylsulfonyl group, isopropylsulfonyl group, butylsulfonyl group, hexylsulfonyl group, cyclohexylsulfonyl group, octylsulfonyl group, 2-ethylhexylsulfonyl group, decanoylsulfonyl group, dodecanoylsulfonyl group, octadecanoylsulfonyl group, cyanomethylsulfonyl group and the like.

Examples of the arylsulfonyl group include a phenylsulfonyl group, 1-naphthylsulfonyl group, 2-naphthylsulfonyl group, 2-chlorophenylsulfonyl group, 2-methylphenylsulfonyl group, 2-methoxyphenylsulfonyl group, 2-butoxyphenylsulfonyl group, 3-chlorophenylsulfonyl group, 3-trifluoromethylphenylsulfonyl group, 3-cyanophenylsulfonyl group, 3-(2-ethylhexyloxy) phenylsulfonyl group, 3-nitrophenylsulfonyl group, 4-fluorophenylsulfonyl group, 4-cyanophenylsulfonyl group, 4-butoxyphenylsulfonyl group, 4-(2-ethylhexyloxy) phenylsulfonyl group, and 4-octadecylphenylsulfonyl group and the like.

An N-alkylsulfamoyl group, N-arylsulfamoyl group, N,N-dialkylsulfamoyl group, N,N-diarylsulfamoyl group and N-alkyl-N-arylsulfamoyl group are included in examples of the sulfamoyl group, in addition to sulfamoyl groups.

Examples of the sulfamoyl group include an N-methylsulfamoyl group, N-ethylsulfamoyl group, N-propylsulfamoyl group, N-butylsulfamoyl group, N-hexylsulfamoyl group, N-cyclohexylsulfamoyl-group, N-octylsulfamoyl group, N-2-ethylhexylsulfamoyl group, N-decylsulfamoyl group, N-octadecylsulfamoyl group, N-phenylsulfamoyl group, N-2-methylphenylsulfamoyl group, N-2-chlorosulfamoyl group, N-2-methoxyphenylsulfamoyl group, N-2-isopropoxyphenylsulfamoyl group, N-2-(2-ethylhexyloxy) phenylsulfamoyl group, N-3-chlorophenylsulfamoyl group, N-3-nitrophenylsulfamoyl group, N-3-cyanophenylsulfamoyl group, N-4-methoxysulfamoyl group, N-4-(2'-ethylhexyloxy) phenylsulfamoyl group, N-4-cyanophenylsulfamoyl group, N-methyl-N-phenylsulfamoyl group, N,N-dimethylsulfamoyl group, N,N-dibutylsulfamoyl group, N,N-diphenylsulfamoyl group, N,N-di-(2-ethylhexyl) sulfamoyl group and the like.

Alkylcarbonyl, arycarbonyl, alkoxycarbonyl and aryloxycarbonyl groups are included in examples of the substituted carbonyl group represented by each of $R^2$ and $R^3$.

Examples of the alkylcarbonyl group include an acetyl group, propanoyl group, butanoyl group, hexanoyl group, octanoyl group, 2-ethylhexanoyl group, decanoyl group, dodecanoyl group, octadecanoyl group, 2-cyanopropanoyl group, and 1,1-dimethylpropanoyl group and the like.

Examples of the arylcarbonyl group include a benzoyl group, o-chlorobenzoyl group, p-chlorobenzoyl group, o-methoxyobenzoyl group, p-methoxyobenzoyl group, and o-methoxyobenzoyl group (toluoyl group).

Examples of the alkoxycarbonyl group include a methoxycarbonyl group, ethoxycarbonyl group, propoxycarbonyl group, butoxycarbonyl group, hexyloxycarbonyl group, 2-ethylhexyloxycarbonyl group, octyloxycarbonyl group, decyloxycarbonyl group, octadecyloxycarbonyl group, phenyloxyethyloxycarbonyl group, phenyloxypropylcarbonyl group, 2,4-di-t-amylphenyloxyethylcarbonyl group, 2,6-di-t-methylcyclohexyloxycarbonyl group, isostearyloxycarbonyl group and the like.

Examples of the aryloxycarbonyl group include a 2-methylphenyloxycarbonyl group, 2-chlorophenyloxycarbonyl group, 2,6-dimethylphenyloxycarbonyl group, 2,4,6-trimethylphenyloxycarbonyl group, 2-methoxyphenyloxycarbonyl group, 2-butoxyphenyloxycarbonyl group, 3-cyanophenyloxycarbonyl group, 3-nitrophenyloxycarbonyl group, 2,2-ethylhexylphenyloxycarbonyl group, 3-(2-ethylhexyloxy) phenyloxycarbonyl group, 4-fluorophenyloxycarbonyl group, 4-chlorophenyloxycarbonyl group, 4-cyanophenyloxycarbonyl group, 4-butoxyphenyloxycarbonyl group and the like.

N-alkylcarbamoyl, N-arylcarbamoyl, N,N$^1$-dialkylcarbamoyl, N,N-diarylcarbamoyl, N-alkyl-N-arylcarbamoyl groups and the like are included in examples of the carbamoyl group, in addition to carbamoyl groups.

Examples of the carbamoyl group include an N-methylcarbamoyl group, N-ethylcarbamoyl group, N-propylcarbamoyl group, N-butylcarbamoyl group, N-hexylcarbamoyl group, N-cyclohexylcarbamoyl group, N-octylcarbamoyl group, N-2-ethylhexylcarbamoyl group, N-decylcarbamoyl group, N-octadecylcarbamoyl group, N-phenylcarbamoyl group, N-2-methylphenylcarbamoyl group, N-2-chlorophenylcarbamoyl group, N-2-methoxyphenylcarbamoyl group, N-2-isopropoxyphenylcarbamoyl group, N-2-(2-ethylhexyloxy) phenylcarbamoyl group, N-3-chlorophenylcarbamoyl group, N-3-nitrophenylcarbamoyl group, N-3-cyanophenylcarbamoyl group, N-4-methoxycarbamoyl group, N-4-(2'-ethylhexyloxy) phenylcarbamoyl group, N-4-cyanophenylcarbamoyl group, N-methyl-N-phenylcarbamoyl group, N,N-dimethylcarbamoyl group, N,N-dibutylcarbamoyl group, N,N-diphenylcarbamoyl group and the like.

Examples of the halogen atom that can be represented by each of $R^2$ and $R^3$ include a fluorine atom, chlorine atom, bromine atom, and the like and fluorine and chlorine atoms are preferred.

Among the groups described above, $R^1$ is particularly preferably a hydrogen atom, an alkyl group having 1 to 8 carbon atoms, or an aryl group having 6 to 10 carbon atoms.

Preferably, $R^2$ and $R^3$ each represents a hydrogen atom, an alkyl group having 1 to 4 carbon atoms, an aryl group having 6 to 10 carbon atoms, analkylsulfonyl group having 1 to 10 carbon atoms, an arylsulfonyl group having 6 to 10 carbon atoms, a sulfamoyl group having 1 to 10 carbon atoms, an alkylcarbonyl group having 1 to 10 carbon atoms, an arylcarbonyl group having 6 to 10 carbon atoms, an alkoxycarbonyl group having 2 to 20 carbon atoms, a carbamoyl group having 1 to 10 carbon atoms, or a cyano group.

In the general formulas (2) to (4), $R^4$ and $R^6$ each independently represents an alkyl group or an aryl group.

Alkyl groups having a substituent and non-substituted alkyl groups are included in examples of the alkyl group represented by each of $R^4$ and $R^6$. The alkyl group is preferably an alkyl group having 1 to 18 carbon atoms. In cases where $R^4$ and $R^6$ represent alkyl groups having a substituent, examples of the substituent include an alkoxy group, aryl group, aryloxy group, alkylthio group, arylthio group, dialkylamino group and the like.

In a case where $R^4$ represents an alkyl group, the alkyl group is preferably a methyl group, an ethyl group, an n-propyl group, an n-butyl group, an isobutyl group, an n-amyl group, a hexyl group, a heptyl group, an n-octyl group, a 2-ethyl-hexyl group, a nonyl group, a decyl group, a hexadecyl group, a 2-methoxyethyl group, a benzyl group or the like. In a case where $R^6$ represents an alkyl group, the alkyl group is preferably a methyl group, an ethyl group, an n-propyl group, an n-butyl group, an isobutyl group, an n-amyl group, an isoamyl group, a hexyl group, a heptyl group, an n-octyl group, a 2-ethyl-hexyl group, a nonyl group, a decyl group, a hexadecyl group, a 2-methoxyethyl group, an ethoxycarbonylmethyl group, a 2-ethyl-hexylcarbonylmethyl group, an aminocarbonylmethyl group, an N,N-dimethylaminocarbonylmethyl group, an N-methylaminocarbonylmethyl group, an isopropyloxyethyl group, a butoxyethyl group, a phenoxyethyl group, a cyanomethyl group, a 3,7-dimethyl-octyl group, a 3,5,5-trimethyl-hexyl group, a benzyl group or the like. Alkyl and alkoxyethyl groups are preferred, and branched alkyl and alkoxyethyl groups are particularly preferred.

Aryl groups having a substituent and non-substituted aryl groups are included in examples of the aryl group represented by each of $R^4$ and $R^6$. The aryl group is preferably an aryl group having 6 to 30 carbon atoms. In cases where $R^4$ and $R^6$ represent aryl groups having a substituent, examples of the substituent include an alkoxy group, nitro group, alkyl group and the like.

In a case where $R^4$ represents an aryl group, the aryl group is preferably a phenyl group, a 4-nitro-phenyl group, a 2-naphthyl group or the like. In a case where $R^6$ represents an aryl group, the aryl group is preferably a phenyl group, a 2-methylphenyl group, a 3-methyl-phenyl group, a 4-methoxy-phenyl group, a 2-naphthyl group or the like.

In the general formula (2), $R^5$ represents an alkyl group, an aryl group, or a heterocyclic group.

Alkyl groups having a substituent and non-substituted alkyl groups are included in examples of the alkyl group represented by $R^5$. Examples of substituents include those mentioned as substituents of the alkyl group represented by each of $R^4$ and $R^6$. The alkyl group represented by $R^5$ is preferably an alkyl group having 1 to 18 carbon atoms, and particularly preferably a methyl group, an ethyl group, an n-propyl group, an n-butyl group, an isobutyl group, an n-amyl group, a hexyl group, a heptyl group, an n-octyl group, a 2-ethyl-hexyl group, a nonyl group, a decyl group, a hexadecyl group, a 2-methoxyethyl group, a benzyl group or the like.

Aryl groups having a substituent and non-substituted aryl groups are included in examples of the aryl group represented by $R^5$. Examples of substituents include those mentioned as substituents of the aryl group represented by each of $R^4$ and $R^6$. The alkyl group represented by $R^5$ is preferably an aryl group having 6 to 30 carbon atoms, and particularly preferably a phenyl group, a 4-nitro-phenyl group, a 2-naphthyl group or the like.

Heterocyclic groups having a substituent and non-substituted heterocyclic groups are included in examples of the heterocyclic group represented by $R^5$. The heterocyclic group may contain a saturated heterocycle or an unsaturated heterocycle. The heterocyclic group is particularly preferably a 2-pyridyl group, a 4-pyridyl group, a 2-pyrimidyl group, a methyl-tetrazoyl group, an ethyl-triazoyl group, a benzothiazoyl group, a benzoxazoyl group or the like.

The aminopyrrole derivative represented by the general formula (1) can be synthesized by conventionally known procedures described in U.S. Pat. Nos. 3,836,541, 3,838, 166, "Synthesis", 1, 51 (1976), and the like.

Specific examples of the aminopyrrole derivative represented by the general formula (1) (exemplified compounds (1-1) to (1-27)) are shown below, but the present invention is not limited by the following specific examples.

General formula (1)

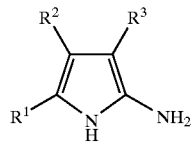

| | $R^1$ | $R^2$ | $R^3$ |
|---|---|---|---|
| 1-1 | —H | —$C_6H_5$ | —H |
| 1-2 | —H | —$C_6H_5$ | —CN |
| 1-3 | —H | —$C_6H_5$ | —$CO_2C_2H_5$ |
| 1-4 | —H | —$C_6H_5$ | 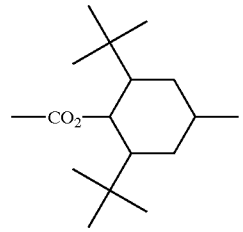 |

-continued
General formula (1)
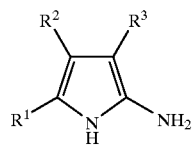
| | R¹ | R² | R³ |
|---|---|---|---|
| 1-5 | —H | 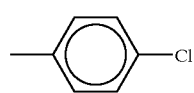 | —CN |
| 1-6 | —H | 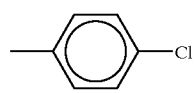 | 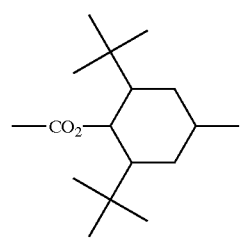 |
| 1-7 | —H | 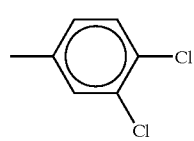 | —CN |
| 1-8 | —H | 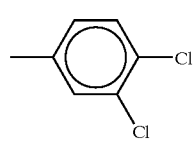 | 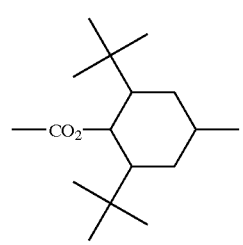 |
| 1-9 | —H | 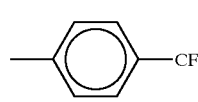 | 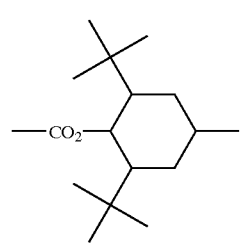 |
| 1-10 | —H | 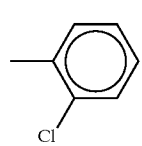 | 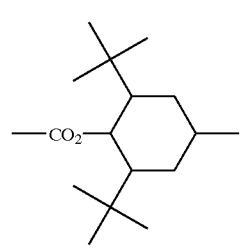 |

-continued

General formula (1)

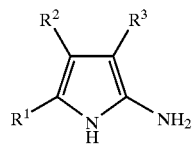

| | $R^1$ | $R^2$ | $R^3$ |
|---|---|---|---|
| 1-11 | —H | —C₆H₄—OCH₃ (p-methoxyphenyl) | —CO₂—(2,6-di-t-butyl-4-methylcyclohexyl) |
| 1-12 | —H | —CN | —CN |
| 1-13 | —H | —CO₂C₂H₅ | —CO₂C₂H₅ |
| 1-14 | —H | —CN | —C₆H₅ |
| 1-15 | —H | —C₆H₅ | —C₆H₅ |
| 1-16 | —CH₃ | —C₆H₅ | —CN |
| 1-17 | —C₆H₄—CH₃ (p-tolyl) | —C₆H₅ | —CN |
| 1-18 | —H | —C₆H₅ | —SO₂C₈H₁₇ |
| 1-19 | —H | —C₆H₅ | —SO₂C₆H₅ |
| 1-20 | —H | —C₆H₅ | —CN |
| 1-21 | —H | —C₆H₅ | —CN |
| 1-22 | —H | —C₆H₅ | —CO₂—(2,6-di-t-butyl-4-methylcyclohexyl) |
| 1-23 | —H | —C₆H₄—Cl (p-chlorophenyl) | —CO₂—(2,6-di-t-butyl-4-methylcyclohexyl) |
| 1-24 | —Cl | —C₆H₅ | —CN |
| 1-25 | —OCH₃ | —C₆H₅ | —CN |
| 1-26 | —OC₆H₅ | —C₆H₄—Cl (p-chlorophenyl) | —CN |
| 1-27 | —SC₄H₉ | —C₆H₅ | —CN |

Specific examples of the reactant represented by the general formula (2) (exemplified compounds (2-1) to (2-35)) are shown below, but the present invention is not limited by the following specific examples.

(2-1) 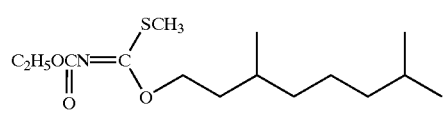
(2-2) 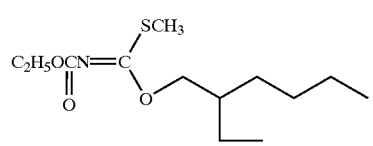
(2-3) 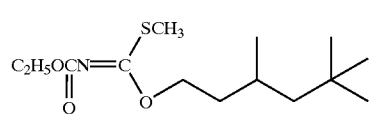
(2-4) 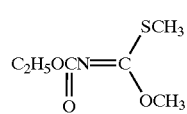
(2-5) 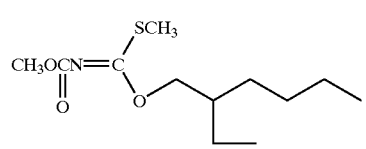
(2-6) 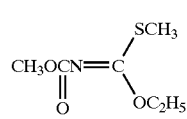
(2-7) 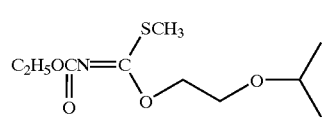
(2-8) 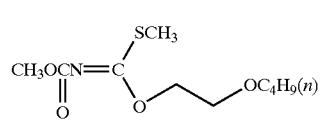
(2-9) 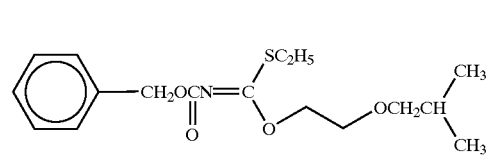
(2-10) 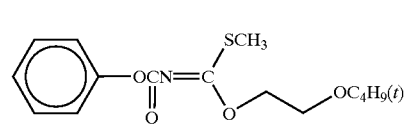
(2-11) 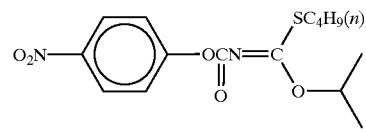
(2-12) 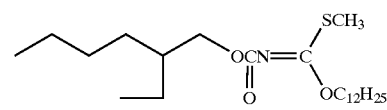
(2-13) 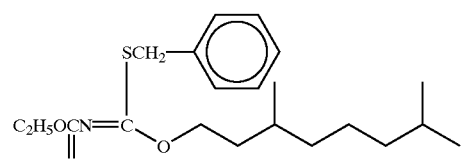
(2-14) 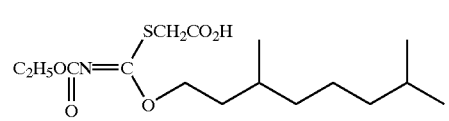
(2-15) 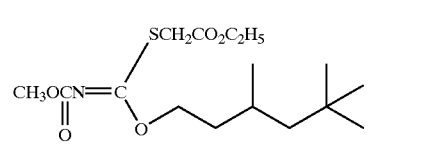
(2-16) 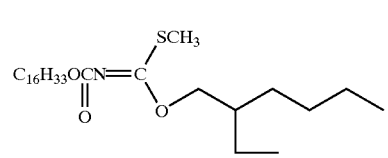
(2-17) 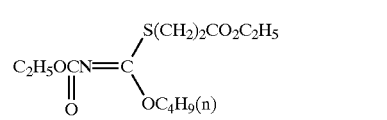
(2-18) 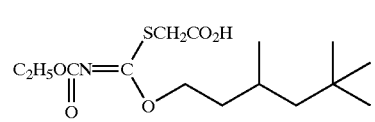
(2-19) 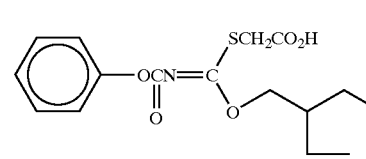
(2-20) 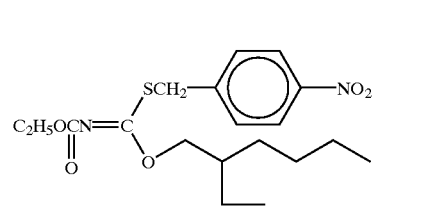

(2-21) 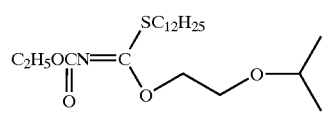
(2-22) 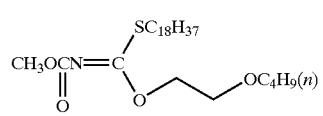
(2-23) 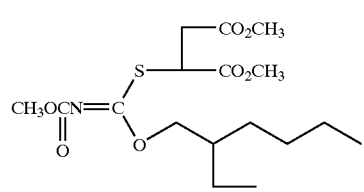
(2-24) 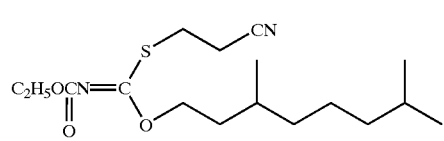
(2-25) 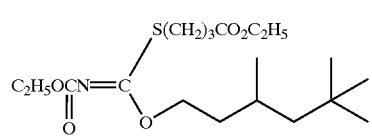
(2-26) 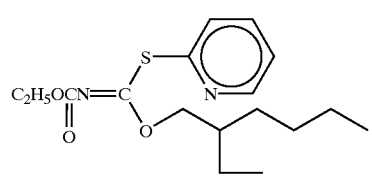
(2-27) 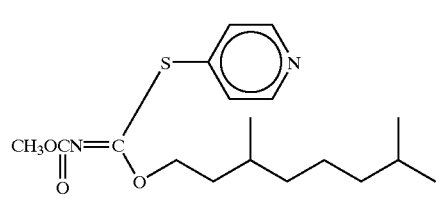
(2-28) 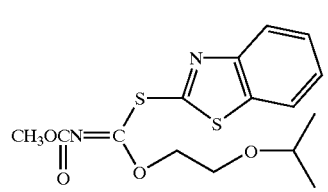
(2-29) 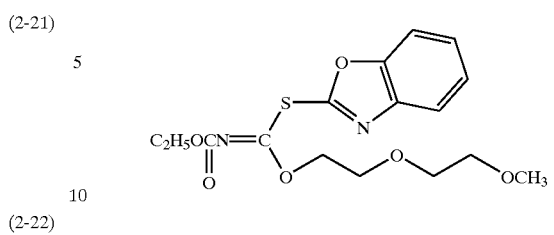
(2-30) 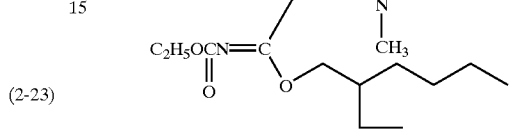
(2-31) 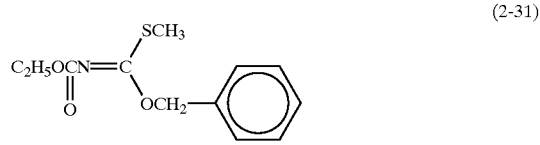
(2-32) 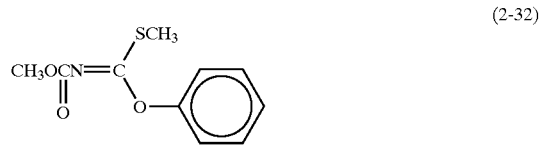
(2-33) 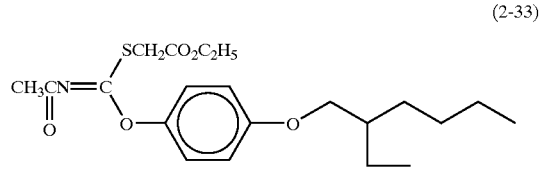
(2-34) 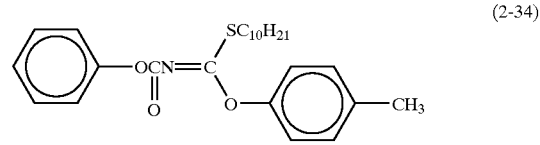
(2-35) 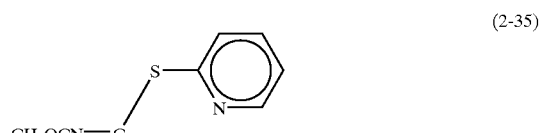
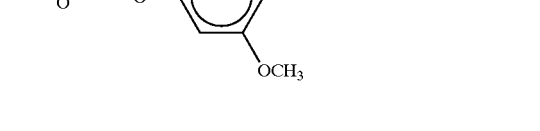
Specific examples of an adduct represented by general formula (3) (exemplified compounds (3-1) to (3-21)) are shown below, but the present invention is not limited by the following specific examples.

| | | General formula (3) 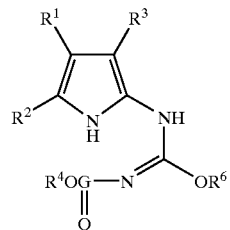 | |
|---|---|---|---|
| | R¹ | R² | R³ |
| 3-1 | —H | —C₆H₅ | —CO₂-[2,6-di-tert-butyl-4-methylcyclohexyl] |
| 3-2 | —H | —C₆H₄-Cl (4-Cl) | —CO₂-[2,6-di-tert-butyl-4-methylcyclohexyl] |
| 3-3 | —H | —C₆H₃-Cl₂ (3,4-diCl) | —CO₂-[2,6-di-tert-butyl-4-methylcyclohexyl] |
| 3-4 | —H | —C₆H₅ | —CN |
| 3-5 | —Cl | —C₆H₅ | —CO₂-[2,6-di-tert-butyl-4-methylcyclohexyl] |
| 3-6 | —Cl | —C₆H₄-Cl (4-Cl) | —CO₂-[2,6-di-tert-butyl-4-methylcyclohexyl] |
| 3-7 | —OCH₃ | —C₆H₄-Cl (4-Cl) | —CN |
| 3-8 | —C₆H₅ | —C₆H₅ | —SO₂-[4-methylcyclohexyl] |

-continued
General formula (3)
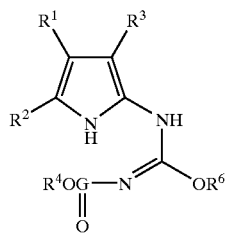
| | R² | R³ | R⁴OG— |
|---|---|---|---|
| 3-9 | —H | 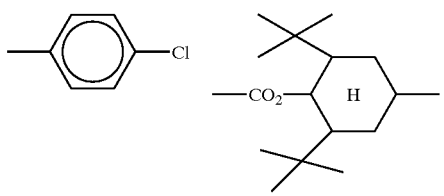 | |
| 3-10 | —H | 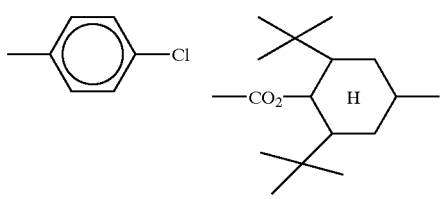 | |
| 3-11 | —H | 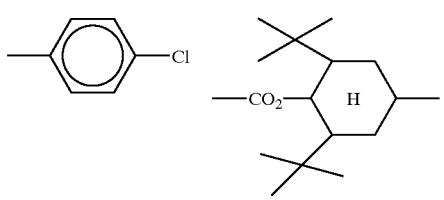 | |
| 3-12 | —CH₃ | —CH₃ | —CO₂C₂H₅ |
| 3-13 | —H |  | —CO₂C₂H₅ |
| 3-14 | —H |  | —CO₂C₂H₅ |
| 3-15 | —H | 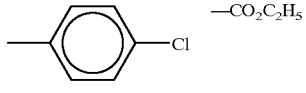 | —CO₂C₂H₅ |
| 3-16 | —H | —CO₂C₂H₅ | —CO₂C₂H₅ |
| 3-17 | —H | 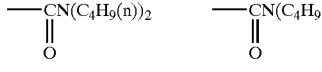 | —CN(C₄H₉(n))₂ with =O |
| 3-18 | —H | —CN |  |

-continued
General formula (3)
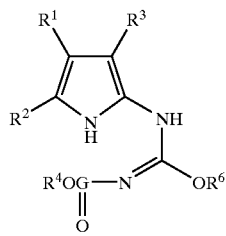
| | R¹ | R² | |
|---|---|---|---|
| 3-19 | —H | —C₆H₅ | —CO₂-[2,6-di-tert-butyl-4-methylcyclohexyl] |
| 3-20 | —H | —C₆H₄-Cl (para) | —CO₂C₂H₅ |
| 3-21 | —SCH₃ | —C₆H₅ | —SO₂CH₃ |
| | R⁴ | R⁶ |
|---|---|---|
| 3-1 | —C₂H₅ | —CH₃ |
| 3-2 | —C₂H₅ | —CH₃ |
| 3-3 | —CH₃ | —CH₃ |
| 3-4 | —C₂H₅ | —C₂H₅ |
| 3-5 | —C₂H₅ | —CH₂CH₂CH(CH₃)CH₂CH₂CH(CH₃)CH₃ |
| 3-6 | —C₂H₅ | —CH₂CH₂CH(CH₃)CH₂CH₂CH(CH₃)CH₃ |
| 3-7 | —C₂H₅ | —CH₂CH(C₂H₅)CH₂CH₂CH₂CH₃ |
| 3-8 | —CH₃ | —CH₂CH₂CH(CH₃)C(CH₃)₃ |
| 3-9 | —C₂H₅ | —CH₂CH₂CH(CH₃)CH₂CH₂CH(CH₃)CH₃ |
| 3-10 | —CH₃ | —CH₂CH₂CH(CH₃)C(CH₃)₃ |
| 3-11 | —C₂H₅ | —CH₂CH₂CH₂OC₄H₉(n) |

-continued

General formula (3)

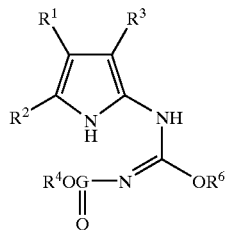

| | | |
|---|---|---|
| 3-12 | 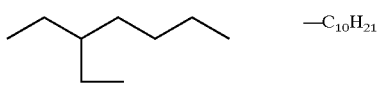 | —$C_{10}H_{21}$ |
| 3-13 |  | —$C_4H_9$(n) |
| 3-14 | —$C_2H_5$ |  |
| 3-15 | —$CH_3$ | 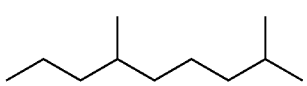 |
| 3-16 | —$C_2H_5$ | —$C_2H_5$ |
| 3-17 | —$CH_3$ | 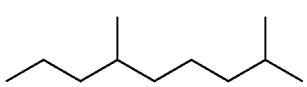 |
| 3-18 | —$C_2H_5$ | 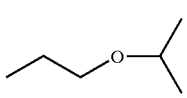 |
| 3-19 | —$C_2H_5$ | 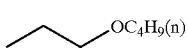 |
| 3-20 | —$C_2H_5$ |  |
| 3-21 | 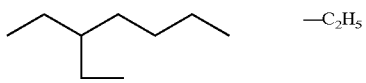 | —$C_2H_5$ |

Specific examples of the pyrrolotriazin-4-one compound represented by the general formula (4) (exemplified compounds (4-1) to (4-21)), which can be prepared by the preparation method of the present invention, are shown below, but the present invention is not limited by the following specific examples.

General formula (4)

| | R¹ | R² | R³ | R⁶ |
|---|---|---|---|---|
| 4-1 | —H | —C₆H₅ | —CO₂-(2,6-di-tert-butyl-4-methylcyclohexyl) | —CH₃ |
| 4-2 | —H | —C₆H₄Cl (4-Cl) | —CO₂-(2,6-di-tert-butyl-4-methylcyclohexyl) | —CH₃ |
| 4-3 | —H | —C₆H₃Cl₂ (3,4-diCl) | —CO₂-(2,6-di-tert-butyl-4-methylcyclohexyl) | —CH₃ |
| 4-4 | —H | —C₆H₅ | —CN | —C₂H₅ |
| 4-5 | —Cl | —C₆H₅ | —CO₂-(2,6-di-tert-butyl-4-methylcyclohexyl) | —CH₂CH(CH₃)CH₂CH₂CH₂CH(CH₃)CH₃ |
| 4-6 | —Cl | —C₆H₄Cl (4-Cl) | —CO₂-(2,6-di-tert-butyl-4-methylcyclohexyl) | —CH₂CH(CH₃)CH₂CH₂CH₂CH(CH₃)CH₃ |
| 4-7 | —OCH₃ | —C₆H₄Cl (4-Cl) | —CN | —CH₂CH(C₂H₅)CH₂CH₂CH₃ |
| 4-8 | —C₆H₅ | —C₆H₅ | —SO₂-cyclohexyl | —CH₂CH₂CH(CH₃)CH₂C(CH₃)₃ |

-continued

General formula (4)

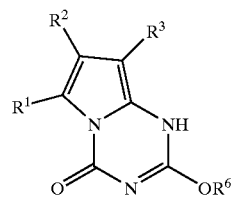

| | R¹ | R² | R³ | R⁶ |
|---|---|---|---|---|
| 4-9 | —H | 4-chlorophenyl | —CO₂—(2,6-di-tert-butyl-4-methylcyclohexyl) | 2,6-dimethylheptyl |
| 4-10 | —H | 4-chlorophenyl | —CO₂—(2,6-di-tert-butyl-4-methylcyclohexyl) | 3,5,5-trimethylhexyl |
| 4-11 | —H | 4-chlorophenyl | —CO₂—(2,6-di-tert-butyl-4-methylcyclohexyl) | —(CH₂)₃OC₄H₉(n) |
| 4-12 | —CH₃ | —CH₃ | —CO₂C₂H₅ | —C₁₀H₂₁ |
| 4-13 | —H | phenyl | —CO₂C₂H₅ | —C₄H₉(n) |
| 4-14 | —H | phenyl | —CO₂C₂H₅ | 2-ethylhexyl |
| 4-15 | —H | 4-chlorophenyl | —CO₂C₂H₅ | 2,6-dimethylheptyl |
| 4-16 | —H | —CO₂C₂H₅ | —CO₂C₂H₅ | —C₂H₅ |
| 4-17 | —H | —C(O)N(C₄H₉(n))₂ | —C(O)N(C₄H₉(n))₂ | 2,6-dimethylheptyl |
| 4-18 | —H | —CN | phenyl | —(CH₂)₃OCH(CH₃)₂ |

-continued

General formula (4)

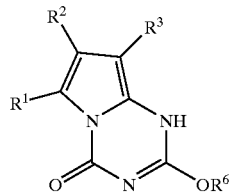

| | $R^1$ | $R^2$ | $R^3$ | $R^6$ |
|---|---|---|---|---|
| 4-19 | —H | —$C_6H_5$ | ![di-tert-butyl cyclohexyl CO2 group] | —$OC_4H_9(n)$ |
| 4-20 | —H | [4-chlorophenyl] | —$CO_2C_2H_5$ | [phenyl] |
| 4-21 | —$SCH_3$ | [4-methylphenyl] | —$SO_2CH_3$ | —$C_2H_5$ |

A scheme of the preparation method of the present invention is shown below.

Method of Preparing Isothiocyanatoformic Acid Ester Derivative

First, a method of preparing an isothiocyanatoformic acid ester ester derivative of the present invention will be described. The isothiocyanatoformic acid ester derivative can be prepared by the following preparation scheme.

Step [1]

ZNCS
General formula (5)

+

$R^6OH$
General formula (6)

General formula (7)

General formula (8)

Step [2]

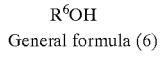
General formula (8)

$M(OH)_n$
General formula (9)

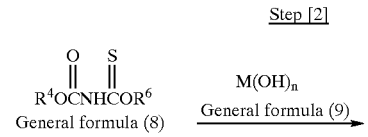
General formula (10)

-continued
Step [3]

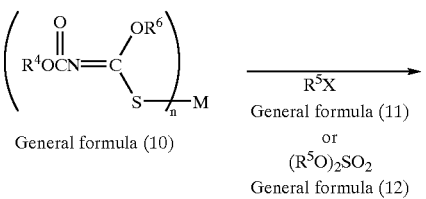
General formula (10)

$R^5X$
General formula (11)
or
$(R^5O)_2SO_2$
General formula (12)

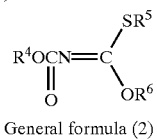
General formula (2)

As shown in the scheme above, the isothiocyanatoformic acid ester derivative of the present invention can be prepared by the step [1], of forming an intermediate represented by general formula (8), step [2], forming an intermediate represented by the general formula (10), and step [3], forming the isothiocyanatoformic acid ester derivative represented by the general formula (2).

These three steps are not necessarily required and the isothiocyanatoformic acid ester derivative can also be prepared using only one of the steps [1], [2] and [3] or two steps selected from the three steps described above in combination with a known step. To obtain the isothiocyanatoformic acid ester derivative, which is preferably used as a reactant for a pyrrolotrizinone compound, with high yield and high purity, all three steps described above are preferably used.

The respective steps will be described below.

Step [1]

The step [1] is a step of preparing the intermediate represented by the general formula (8) by adding an isothiocyanic acid salt represented by general formula (5) a hydroxy derivative represented by general formula (6), and further adding a chloroformic acid derivative represented by general formula (7).

In the general formula (5), Z represents a sodium atom or a potassium atom. In the general formulas (6), (7) and (8), $R^4$ and $R^6$ are as defined for the general formula (2).

An amount (mol) of the isothiocyanic acid salt represented by the general formula (5) is preferably 1–5 times, and more preferably 1–3 times, an amount of the chloroformic acid derivative represented by the general formula (6).

An amount (mol) of the hydroxy derivative represented by the general formula (7) is preferably 0.5–3 times, and more preferably 0.5–1.5 times, an amount of the chloroformic acid derivative represented by the general formula (6).

In the step [1], the intermediate represented by the general formula (8) can be prepared by dissolving the isothiocyanic acid salt represented by the general formula (5) and the hydroxy derivative represented by the general formula (6) in a reaction solvent, and adding the chloroformic acid derivative represented by the general formula (7) dropwise, thus causing a reaction.

Suitable examples of the reaction solvent include acetonitrile, acetone, tetrahydrofuran and the like. Among these reaction solvents, acetonitrile and acetone are preferred.

The reaction temperature in the step [1] is preferably from −25 to 40° C., and more preferably from −5 to 25° C.

In the step [1] an isothiocyanatoformic acid ester ($R^4$OOCNCS) formed by the reaction between the isothiocyanic acid salt represented by the general formula (5) and the chloro formic acid derivative represented by the general formula (6) reacts with the hydroxy derivative represented by the general formula (7) immediately, because of prior colocalization of the isothiocyanic acid salt represented by the general formula (5) and the hydroxy derivative represented by the general-formula (6). Therefore, decomposition of the isothiocyanatoformic acid ester ($R^4$OCNCS) is prevented. As a result, the yield of the intermediate represented by the general formula (8) is enhanced as compared with a conventional preparation method.

Step [2]

The step [2] is a step of preparing the intermediate represented by the general formula (10) from the intermediate represented by the general formula (8) and a compound represented by general formula (9).

In the general formula (9), M represents an alkali metal atom, an alkali earth metal atom, an aluminum atom, or a magnesium atom. In the general formula (10), $R^4$ and $R^6$ are as defined for the general formula (2).

The alkali metal atom is preferably a lithium atom, a sodium atom, a potassium atom, or a cesium atom.

The alkali earth metal atom is preferably a calcium atom or a barium atom.

In the step [2], the intermediate represented by the general formula (10) can be prepared by dissolving the compound represented by the general formula (9) in a reaction solvent, and adding the intermediate represented by the general formula (8), thus precipitating the intermediate represented by the general formula (10) as crystals.

Suitable examples of the reaction solvent include water, methanol, ethanol, acetonitrile, acetone, tetrahydrofuran and the like. Among these reaction solvents, methanol and ethanol are preferred.

An amount (mol) of the compound represented by the general formula (9) is preferably 1–5 times-an amount of the intermediate represented by the general formula (8).

To accelerate crystallization, a compound represented by general formula MY (M is as defined for the general formula (9), and Y represents a halogen atom) may be added. An amount (mol) of the compound represented by the general formula MY is preferably 1–10 times the amount of the intermediate represented by the general formula (8).

In the step [2], the compound represented by the general formula (10) can be obtained as crystals by reacting the intermediate represented by the general formula (8) with the compound represented by the general formula (9), and can be purified by means of recrystallization or the like.

Step [3]

The step [3] is a step of preparing the isothiocyanatoformic acid ester derivative represented by the general formula (2) by reacting the intermediate represented by the general formula (10) with an alkylating agent represented by general formula (11) or (12).

In the general formula (11), X represents a halogen atom or $SO_3$Ar. Ar represents a substituted or non-substituted aryl group.

Preferred examples of the halogen atom include a chloride atom, a bromine atom, and an iodine atom.

In the general formulas (11) and (12), $R^5$ is as defined for the general formula (2).

An amount (mol) of the alkylating agent represented by the general formulas (11) and (12) is preferably 1–3 times, and more preferably 1–1.5 times, an amount of the intermediate represented by the general formula (10).

In the step [3], the isothiocyanatoformic acid ester derivative represented by the general formula (2) can be prepared by suspending the intermediate represented by the general formula (10) in a reaction solvent, and adding the alkylating agent represented by the general formulas (11) or (12) dropwise.

Suitable examples of the reaction solvent include acetonitrile, acetone, dimethylformamide, dimethylacetylamide, tetrahydrofuran, dimethyl sulfoxide, and alcohol (e.g. methanol, ethanol, isopropanol, propanol, n-butanol, t-butanol, etc.). Among these reaction solvents, acetonitrile, ethyl acetate, butyl acetate, benzene, toluene, dimethylformamide, dimethylacetylamide, tetrahydrofuran, and dimethyl sulfoxide are preferred.

The reaction temperature in the step [3] is preferably from −25 to 40° C., and more preferably from −5 to 25° C.

A method of synthesizing the pyrrolotriazinone compound in the present invention will be described below. The pyrrolotriazinone compound can be prepared through the following preparation scheme.

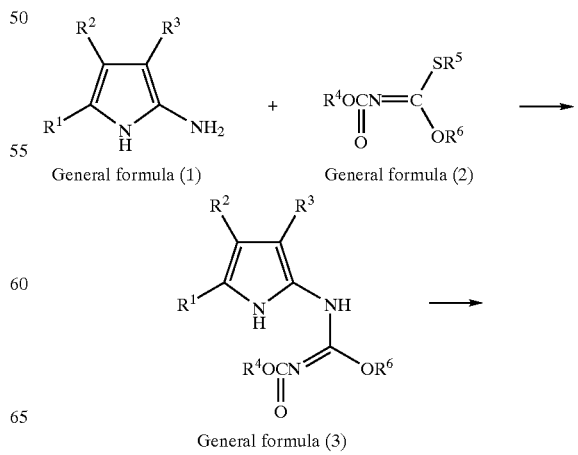

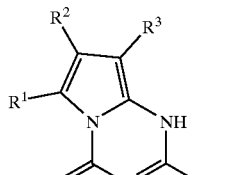

General formula (4)

Respective steps will be described below.

Addition Step

The addition step is a step of reacting the aminopyrrole derivative represented by the general formula (1) with the reactant represented by the general formula (2) to form the adduct represented by the general formula (3). For example, a reaction can be caused to proceed by uniformly dissolving or suspending the aminopyrrole derivative represented by the general formula (1) and the reactant represented by the general formula (2), optionally adding an acid, and heating.

The reaction temperature in the addition step is preferably not less than −5° C. and not more than the boiling point of a solvent being used, and more preferably not less than 30° C. and not more than 80° C. in view of ease of operation.

The aminopyrrole derivative represented by the general formula (1) is preferably dissolved in a 1.0- to 50-fold amount (by weight) of an organic solvent, and more preferably dissolved in a 5.0- to 30-fold amount (by weight) of the organic solvent.

The organic solvent used in the addition step is preferably inert with respect to the reactant represented by the general formula (2), and is preferably anhydrous. Examples of the organic solvent include acetonitrile, acetone, ethyl acetate, butyl acetate, benzene, toluene, dimethylformamide, dimethylacetylamide, tetrahydrofuran, dimethyl sulfoxide, and alcohol (e.g. methanol, ethanol, isopropanol, propanol, n-butanol, t-butanol, etc.). Among these organic solvents, acetonitrile, acetone, tetrahydrofuran, ethyl acetate, butyl acetate, and toluene are preferred.

In the addition step, an amount (mol) of the reactant represented by the general formula (2) is preferably 1.0–5.0 times, and more preferably 1.0–2.0 times, an amount of the aminopyrrole derivative represented by the general formula (1).

In the addition step, the reaction can be accelerated if an acid or a salt thereof or a base is allowed to exist in the reaction, which is preferable. Examples of the acid or salt thereof include substituted or non-substituted alkylcarboxylic acid (preferably $C_{1-18}$ alkylcarboxylic acid) and salts thereof (alkali metal or alkali earth metal, such as Na, K, etc.); substituted or non-substituted arylcarboxylic acid (preferably $C_{6-35}$ alkylcarboxylic acid) and salts thereof (alkali metal or alkali earth metal, such as Na, K, etc.); substituted or non-substituted alkylsulfonic acid (preferably $C_{1-18}$, alkylsulfonic acid) and salts thereof (alkali metal or alkali earth metal, such as Na, K, etc., or an organic base such as pyridinetriethylamine, 1,8-diazobicyclo[5.4.0]undece-7-ene (DBU), etc.); substituted or non-substituted arylsulfonic acid (preferably $C_{6-35}$ arylsulfonic acid) and salts thereof (alkali metal or alkali earth metal, such as Na, K, etc., an organic base such as pyridinetriethylamine, DBU, etc.); and Lewis acids (e.g. $BF_4$, $ZnCl_2$, $ZnCl_4$, $AlCl_3$, etc.). Examples of the base include organic bases (e.g. triethylamine, DBU, etc.), hydride (e.g. NaH, KH, $CaH_2$, etc.), andalcoholates (e.g. NaOMe, NaOEt, KO(t)Bu, etc.).

Among these, an acid is preferred. Among acids, a substituted or non-substituted alkylcarboxylic acid (preferably $C_{1-18}$ alkylcarboxylic acid), a substituted or non-substituted arylcarboxylic acid (preferably $C_{6-35}$ alkylcarboxylic acid), a substituted or non-substituted alkylsulfonic acid (preferably $C_{1-18}$ alkylsulfonic acid), and a substituted or non-substituted arylsulfonic acid (preferably $C_{6-35}$ arylsulfonic acid) are preferred, and trifluoroacetic acid and methanesulfonic acid are particularly preferred.

The amount of the acid or salt thereof or base is preferably not less than 0.1 mmol and not more than 3.0 mmol, and more preferably not less than 0.1 mmol and not more than 1.0 mmol, for 1.0 mol of the aminopyrrole derivative represented by the general formula (1). These acids or salts thereof or bases may be used alone or in a combination thereof. When using two or more kinds thereof, the total amount thereof is preferably within the range described above.

Preferably, when using the acid or salt thereof or base, the acid is uniformly dissolved or suspended in a solvent, together with the aminopyrrole derivative and the reactant.

After completion of the reaction, the adduct represented by the general formula (3) can be obtained by removing by-products and solvent from the resulting reaction mixture. Generally, substances formed as by-products in the addition step are slightly soluble. Thus, the adduct can be purified by recrystallizing from a suitable solvent, making use of a difference in solubility in an organic solvent between the by-products and the adduct.

The adduct can be transferred to the following cyclization step as is without being isolated from a reaction system.

Cyclization Step

In the cyclization step, the adduct represented by the general formula (3) is cyclized to form the pyrrolotriazin-4-one represented by the general formula (4). For example, a reaction can be caused to proceed by uniformly dissolving the adduct represented by the general formula (3) in a solvent, optionally adding an acid, and then heating.

The reaction temperature in the cyclization step is preferably not less than −5° C. and not more than the boiling point of the solvent being used, and more preferably not less than 10° C. and not more than 85° C. in view of ease of operation.

The adduct represented by the general formula (3) is preferably dissolved in a 1.0- to 50-fold amount (by weight) of an organic solvent, and more preferably dissolved in a 5.0- to 30-fold amount (by weight) of the organic solvent.

Examples of the organic solvent include acetonitrile, acetone, ethyl acetate, butyl acetate, benzene, toluene, dimethylformamide, dimethylacetylamide, tetrahydrofuran, dimethyl sulfoxide, and alcohol (e.g. methanol, ethanol, isopropanol, propanol, n-butanol, t-butanol, etc.). Among these organic solvents, acetonitrile, acetone, tetrahydrofuran, methanol, ethanol, isopropanol, propanol and the like are preferred.

In a case where the adduct represented by the general formula (3) is transferred to the cyclization step without isolation, the same organic solvent as that used in the addition step can be used. For example, acetonitrile, acetone and tetrahydrofuran are organic solvents which can be preferably used in both steps.

In the cyclization step, the reaction can be accelerated if an acid or a salt thereof or a base is allowed to exist in the reaction, which is preferable. Examples of the acid or salt thereof include substituted or non-substituted alkylcarboxylic acid (preferably $C_{1-18}$ alkylcarboxylic acid) and salts thereof (alkali metal or alkali earth metal, such as Na, K, etc., or an organic base such as pyridinetriethylamine, DBU, piperidine, etc.); substituted or non-substituted alkylsulfonic acid (preferably $C_{1-18}$ alkylsulfonic acid) and salts thereof (alkali metal or alkali earth metal, such as Na, K, etc., or an organic base such as pyridinetriethylamine, DBU, etc.); substituted or non-substituted arylsulfonic acid (preferably $C_{6-35}$ arylsulfonic acid) and salts thereof (alkali metal or alkali earth metal, such as Na, K, etc., or an organic base such as pyridinetriethylamine, DBU, etc.); and Lewis acids (e.g. $BF_4$, $ZnCl_2$, $ZnCl_4$, $AlCl_3$, etc.). Examples of the base include organic bases (e.g. triethylamine, DBU, etc.), hydride (e.g. NaH, KH, $CaH_2$, etc.), and alcoholates (e.g. NaOMe, NaOEt, KO(t)Bu, etc.).

Among these, an organic base (e.g. triethylamine, DBU, etc.), an alcoholate (e.g. NaOMe, NaOEt, KO(t)Bu, etc.), or a substituted or non-substituted alkylcarboxylic acid or a salt thereof (e.g. acetic acid, potassium acetate, sodium acetate, piperidine acetate, etc.) is preferred.

The amount of the acid or salt thereof or base is preferably not less than 0.1 mol and not more than 3.0 mol for 1.0 mol of the adduct represented by the general formula (3). These acids or salts thereof or bases may be used alone or in a combination thereof. When using two or more kinds thereof, the total amount thereof is preferably within the range described above.

In a case where the adduct represented by the general formula (3) is transferred to the cyclization step without being isolated, the acid or salt thereof or base is added to a reaction mother liquor of in the addition step after completion of the addition reaction. In this case, the acid or salt thereof or base is preferably added an amount of not less than 1.0 mol and not more than 3.0 mol, based on a stock amount of the aminopyrrole derivative represented by the general formula (1).

After completion of the cyclization reaction, the reaction mixture is cooled, thereby making it possible to precipitate the pyrrolotriazin-4-one compound represented by the general formula (4) and to isolate the same by filtration or the like. Crude crystals obtained by filtration can be purified by recrystallizing from a suitable solvent.

EXAMPLES

The following Examples further illustrate the present invention in detail, but the present invention is not limited by these Examples.

Example 1

Preparation Example of exemplified compound (2-1), an isothiocyanatoformic acid ester derivative The exemplified compound (2-1) and Preparation Example thereof are shown below.

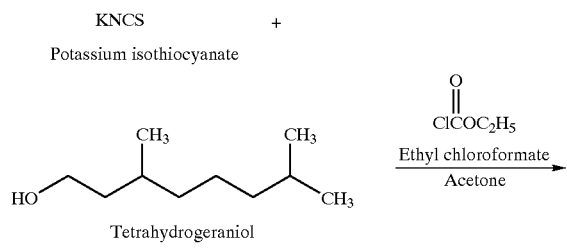

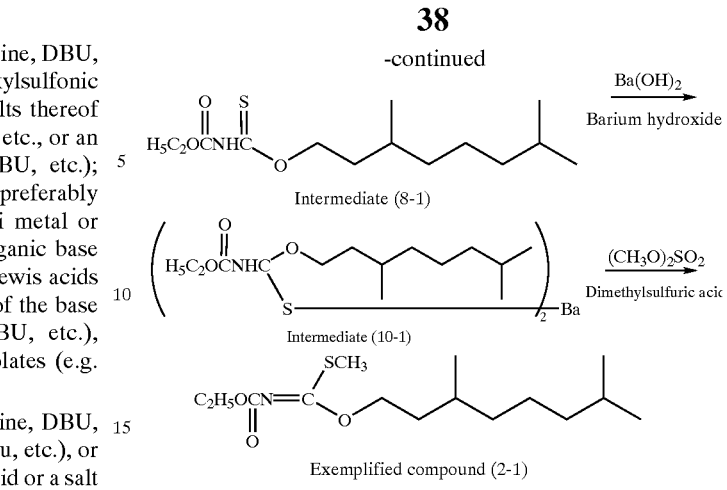

1) Preparation of Intermediate (10-1)

48.5 g (0.5 mol) of potassium isothiocyanate (KNCS) and 71 g (0.45 mol) of tetrahydrogeraniol (3,7-dimethyl-1-octanol) were dissolved in 250 ml of acetone. The solution was cooled to an inner temperature of 5° C., and then 48.5 g (0.45 mol) of ethyl chloroformate was added dropwise over one hour such that the inner temperature did not rise to 15° C. or higher. A reaction proceeded for three hours with the reaction solution in the cooled state, the inner temperature was then returned to room temperature, and the solution was left to stand for 24 hours.

Then, 94 g (0.3 mol) of a barium hydroxide ($Ba(OH)_2$) hydrate was dissolved in 500 ml of water, the reaction solution was added to this aqueous solution, and crystals were precipitated. The resulting crystals were collected by filtration and then washed with water until an alkali component was removed. After drying, 114 g (0.16 mol) of intermediate (10-1) was obtained as white crystals.

The yield of the intermediate (10-1) was 71%, calculated in terms of tetrahydrogeraniol.

The purity of the intermediate (10-1) was measured by gas chromatography, and was at least 98%.

The intermediate (10-1) was neutralized to form an intermediate (8-1), and then structural analysis was conducted by $^1$H-NMR (solvent: $CDCl_3$, 300MHz, TMS standard). Results data are shown below.

$^1$H-NMR [δ, ppm]: 8.13 (1H, NH), 4.58 (2H, —OCH$_2$CH$_2$), 4.21 (2H, —OCH$_2$CH$_3$), 2.37 (3H, —SCH$_3$)

2) Preparation of Exemplified Compound (2-1)

75 g (0.115 mol) of the intermediate (10-1) obtained in 1) was dissolved in acetone. This reaction solution was cooled to 15° C., and then 30 g (0.24 mol) of dimethylsulfuric acid serving as an alkylating agent was added dropwise over 15 minutes. Thereafter, a reaction was conducted for one hour, and then the reaction solution was filtered to remove an inorganic component. The resulting filtrate was concentrated under reduced pressure and this concentrate was extracted by adding 100 ml of ethyl acetate and 100 ml of water. An organic layer was concentrated under reduced pressure to obtain 64 g (0.21 mol) of the exemplified compound (2-1) of the isothiocyanatoformic acid ester derivative as a light yellow oily component.

The yield of the exemplified compound (2-1) was 91%.

The purity of the exemplified compound (2-1) was measured by gas chromatography, and was 98%.

Structural analysis of the exemplified compound (2-1) was conducted by $^1$H-NMR (solvent: $CDCl_3$, 300 MHz, TMS standard). Results data are shown below. $^1$H-NMR (δ, ppm): 4.36 (2H, —OCH$_2$CH$_2$), 4.23 (2H, —OCH$_2$CH$_3$), 2.37 (3H, —SCH$_3$)

Comparative Example 1

Preparation Example of comparative compound (2'-1), an isothiocyanatoformic acid ester derivative The exemplified compound (2'-1) and Preparation Example thereof are shown below.

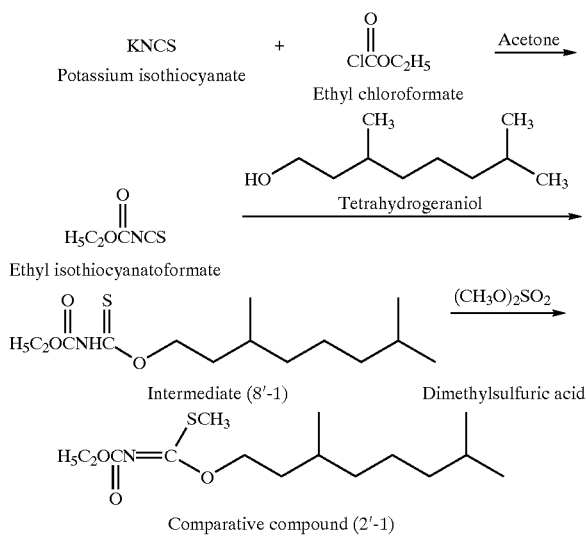

Comparative compound (2'-1)

1) Preparation of Intermediate (8'-1)

48.5 g (0.5 mol) of potassium isothiocyanate (KNCS) was dissolved in 250 ml of acetone. This solution was cooled to an inner temperature of 5° C., and then 48.5 g (0.45 mol) of ethyl chloroformate ($ClCOOC_2H_5$) was added dropwise over one hour such that the inner temperature did not rise to 15° C. or higher. Thereafter, 71 g (0.45 mol) of tetrahydrogeraniol was added to the reaction solution and the solution was left to stand at room temperature for 24 hours. 5 g of activated carbon was added to the reaction solution and the solution, was filtered to remove the activated carbon and an inorganic component. The resulting filtrate was concentrated under reduced pressure to obtain 95 g of an intermediate (8'-1) as a yellow oily product.

The purity of the intermediate (8'-1) was measured by gas chromatography, and was 55%.

2) Preparation of Comparative Compound (2'-1)

95 g (0.33 mol) of the intermediate (8'-1) obtained in 1) and 50 g (1.36 mol) of potassium carbonate were dissolved in 500 ml of acetone. This reaction solution was cooled to 15° C., and then 46 g (0.36 mol) of dimethylsulfuric acid serving as an alkylating agent was added dropwise over 30 minutes. Thereafter, a reaction was conducted for two hours, and then the reaction solution was filtered to remove an inorganic component. The resulting filtrate was concentrated under reduced pressure and this concentrate was extracted by adding 500 ml of ethyl acetate and 500 ml of water. An organic layer was concentrated under reduced pressure to obtain 90 g of the comparative compound (2'-1) of the isothiocyanatoformic acid ester derivative as a light yellow oily component.

The purity of the comparative compound (2'-1) was measured by gas chromatography, and was 40%.

It was confirmed from the results described above that with the preparation method of the present invention, an isothiocyanatoformic acid ester derivative can be prepared at higher yield and higher purity than with the preparation method of the Comparative Example.

Example 2
Synthesis of Exemplified Compound (4-9)

To a reaction solution prepared by suspending 85 g (0.19 mol) of an aminopyrrole, exemplified compound (1-6), and 71 g (0.22 mol) of the exemplified compound (2-1) in 150 ml of acetonitrile, 0.5 g (5 mmol) of methanesulfonic acid was added. Then the reaction solution was heated to 55–60° C. and further stirred for 24 hours.

20 ml of acetic acid was added to the reaction solution, and then 15 g of 28% sodium methoxide was added. Then the reaction solution was heated to 55–60° C. and further stirred for six hours. The reaction solution was cooled to 10° C.–15° C. and stirred for one hour. Crystals precipitated from the reaction solution were filtered and recrystallized from ethanol to obtain 51 g (yield: 47%) of the exemplified compound (4-9) as white crystals.

Data ($\delta$, ppm) of $^1$H-NMR (solvent: $CDCl_3$, TMS standard, 300 MHz) for the resulting compound were:

10.4 (s, 1H), 7.2–7.45 (m, 5H), 5.85 (s, 1H), 4.6 (m, 2H)

Example 3
Synthesis of Exemplified Compound (4-2)

To a reaction solution prepared by suspending 80 g (0.18 mol) of the aminopyrrole, exemplified compound (1-6), and 42 g (0.237 mol) of the exemplified compound (2-4) in 200 ml of acetonitrile, 0.5 g (5 mmol) of methanesulfonic acid was added. Then the reaction solution was heated to 55–60° C. and further stirred for 24 hours. The reaction solution was cooled to room temperature and precipitated crystals were filtered. The resulting crude crystals were recrystallized from ethanol to obtain 75 g (yield: 73%) of the exemplified compound (3-2) as light yellow crystals.

Data ($\delta$, ppm) of $^1$H-NMR (solvent: $CDCl_3$, TMS standard, 300 MHz) for the resulting compound were:

9.3 (s, 1H), 7.2–7.37 (m, 4H), 6.25 (d, 1H), 5.85 (s, 1H), 4.3 (q, 2H), 4.15 (s, 3H), 1.35 (t, 3H)

To a suspension prepared by suspending 65 g (0.114 mol) of the resulting exemplified compound (3-2) in 200 ml of ethanol, 25 g (0.13 mol) of 28% sodium methoxide was added. Then the suspension was heated to 35–40° C. and further stirred for one hour. Water was poured into this reaction solution and this solution was neutralized with hydrochloric acid. Then, after extracting with 300 ml of ethyl acetate, an organic layer was concentrated under reduced pressure. To this solidified concentrate, 250 ml of methanol was added, after which heating at reflux was performed for one hour. After cooling to room temperature, precipitated crystals were filtered to obtain 48 g (yield: 80%) of an exemplified compound (4-2) as white crystals.

Data ($\delta$, ppm) of $^1$H-NMR (solvent: $CDCl_3$, TMS standard, 300 MHz) for the resulting compound were:

10.2 ($\delta$, 1H), 7.2–7.4 (m, 5H), 5.9 (s, 1H), 4.17 (s, 3H)

With the present invention, a pyrrolotriazin-4-one compound can be prepared at high yield by a simple operation. Also, with the present invention, a novel isothiocyanatoformic acid ester derivative, which can be used preferably as a reactant for synthesis of a pyrrolotriazinone compound, can be provided, and a method of preparing the isothiocyanatoformic acid ester derivative at high purity and high yield can be provided.

What is claimed is:

1. A method of preparing an isothiocyanatoformic acid ester product representative by the following formula (2):

Formula (2)

$$R^4OCN=C \begin{matrix} SR^5 \\ \\ OR^6 \end{matrix}$$

$$\parallel$$
$$O$$

in which: $R^4$ represents a substituted or non-substituted alkyl group, or a substituted or non-substituted aryl group; $R^5$ represents a substituted or non-substituted alkyl group, a substituted or non-substituted aryl group, or a substituted or non-substituted heterocyclic group; and $R^6$ represents a substituted or non-substituted alkyl group having at least 3 carbon atoms, the method comprising:

preparing a first intermediate represented by the following formula (8) by mixing an isothiocyanic acid salt represented by the following formula (5) and a hydroxy derivative represented by the following formula (6), and then adding a chloroformic acid derivative represented by the following formula (7);

preparing a second intermediate represented by the following formula (10) from the first intermediate and a compound represented by the following formula (9); and reacting the second intermediate with an alkylating agent represented by one of the following formulas (11) and (12) for preparing the isothiocyanatoformic acid ester product:

ZNCS  Formula (5)

$R^6$OH  Formula (6)

$$\underset{ClCOR^4}{\overset{O}{\|}}$$  Formula (7)

$$\underset{R^4OCNHCOR^6}{\overset{O\quad S}{\|\quad\|}}$$  Formula (8)

M(OH)$_n$  Formula (9)

$$\left( \underset{R^4OCN=C}{\overset{O}{\|}} \underset{S}{\overset{OR^6}{\diagup}} \right)_n M$$  Formula (10)

$R^5X$  Formula (11)

$(R^5O)_2SO_2$  Formula (12)

wherein, in the formula (5), Z represents a sodium atom or a potassium atom, in the formulas (9) and (10), M represents an alkali metal atom, an alkali earth metal atom, an aluminum atom or a magnesium atom, n represents an integer selected from 1 to 3, and, in the formula (11), X represents a halogen atom or $SO_3Ar$, and Ar represents a substituted or non-substituted aryl group, and wherein the second intermediate represented by the formula (10) is obtained as crystals.

2. The method of claim 1, wherein in preparing the first intermediate represented by formula (8), the intermediate represented by the formula (8) is prepared by dissolving in a reaction solvent the isothiocyanic acid salt represented by the formula (5) and the hydroxy derivative represented by the formula (6), and then adding dropwise the chloroformic acid derivative represented by the formula (7), thus causing a reaction.

3. The method of claim 1, wherein in preparing the first intermediate represented by the formula (8), an amount (mol) of the isothiocyanic acid salt represented by the formula (5) is 1 to 5 times an amount of the hydroxy derivative represented by the formula (6).

4. The method of claim 1, wherein in preparing the first intermediate represented by the formula (8), an amount (mol) of the isothiocyanic acid salt represented by the formula (5) is 1 to 3 times an amount of the hydroxy derivative represented by the formula (6).

5. The method of claim 1, wherein in preparing the first intermediate represented by the formula (8), an amount (mol) of the chloroformic acid derivative represented by the formula (7) is 0.5 to 3 times an amount of the hydroxy derivative represented by the formula (6).

6. The method of claim 1, wherein in preparing the first intermediate represented by the formula (8), an amount (mol) of the chloroformic acid derivative represented by the formula (7) is 0.5 to 1.5 times an amount of the hydroxy derivative represented by the formula (6).

7. The method of claim 1, wherein in preparing the first intermediate represented by the formula (8), a solvent selected from the group consisting of acetonitrile, acetone, and tetrahydrofuran is used as a reaction solvent.

8. The method of claim 1, wherein in preparing the first intermediate represented by the formula (8), a reaction temperature thereof is in a range from −25 to 40° C.

9. The method of claim 1, wherein in preparing the second intermediate represented by the formula (10), an amount (mol) of the compound represented by the formula (9) is 1 to 5 times an amount of the first intermediate represented by the formula (8).

10. The method of claim 1, wherein in preparing the second intermediate represented by the formula (10), a solvent selected from the group consisting of water, methanol, ethanol, acetonitrile, acetone, and tetrahydrofuran is used as a reaction solvent.

11. The method of claim 1, wherein in reacting the second intermediate represented by the formula (10) with the alkylating agent represented by one of the formulas (11) and (12), suspending the intermediate represented by the formula (10) in a reaction solvent and then adding dropwise the alkylating agent represented by the formulas (11) or (12) are included in order to obtain the isothiocyanatoformic acid ester represented by the formula (2).

12. The method of claim 1, wherein in reacting the second intermediate represented by the formula (10) with the alkylating agent represented by one of the formulas (11) and (12), an amount (mol) of at least one of the alkylating agent represented by one of the formulas (11) and (12) is 1 to 3 times an amount of the second intermediate represented by the formula (10).

13. The method of claim 1, wherein in reacting the second intermediate represented by the formula (10) with the alkylating agent represented by one of the formulas (11) and (12), an amount (mol) of at least one of the alkylating agent represented by one of the formulas (11) and (12) is 1 to 1.5 times an amount of the second intermediate represented by the formula (10).

14. The method of claim 1, wherein in reacting the second intermediate represented by the formula (10) with the alkylating agent represented by one of the formulas (11) and (12), a solvent selected from the group consisting of acetonitrile, acetone, dimethylformamide, dimethylacetylamide, tetrahydrofuran, dimethyl sulfoxide, and alcohol is used as a reaction solvent.

* * * * *